United States Patent [19]

Ahmad

[11] Patent Number: 5,344,962
[45] Date of Patent: Sep. 6, 1994

[54] INTERMEDIATES IN THE SYNTHESIS OF AN OPTICALLY ACTIVE CYCLOBUTANE NUCLEOSIDE

[75] Inventor: Saleem Ahmad, Plainsboro, N.J.

[73] Assignee: E. R. Squibb & Sons, Inc., Princeton, N.J.

[21] Appl. No.: 58,088

[22] Filed: May 10, 1993

Related U.S. Application Data

[60] Division of Ser. No. 692,752, Apr. 29, 1991, Pat. No. 5,233,076, which is a continuation-in-part of Ser. No. 528,626, May 24, 1990, abandoned.

[51] Int. Cl.$^5$ .............................................. C07C 69/74
[52] U.S. Cl. ................................... 560/123; 549/333; 549/342
[58] Field of Search ............... 560/123; 549/323, 242, 549/333, 454, 342

[56] References Cited

U.S. PATENT DOCUMENTS

| | | | |
|---|---|---|---|
| 3,317,586 | 5/1967 | Burpitt et al. | 260/468 |
| 4,855,466 | 8/1989 | Zahler et al. | 549/546 |
| 4,918,075 | 4/1990 | Zahler et al. | 524/262 |
| 5,064,961 | 11/1991 | Bisacchi et al. | 544/276 |
| 5,198,583 | 3/1993 | Bisacchi et al. | 564/158 |
| 5,233,076 | 8/1993 | Ahmad | 560/106 |
| 5,235,052 | 8/1993 | Pariza et al. | 544/276 |
| 5,256,806 | 10/1993 | Bisacchi et al. | 556/419 |

FOREIGN PATENT DOCUMENTS

| | | |
|---|---|---|
| 335355 | 10/1989 | European Pat. Off. |
| 358154 | 3/1990 | European Pat. Off. |
| 366059 | 5/1990 | European Pat. Off. |
| 452729 | 10/1991 | European Pat. Off. |

OTHER PUBLICATIONS

Slusarchyk et al., "Synthesis of SQ-33,054 . . . " Tetrahedron Letters, vol. 30, No. 7, pp. 6453–6456 (1989).

Ichikawa et al. "Enantio- and Diastereo-selective . . . " J. Chem. Soc., Chem. Commun., 1989, pp. 1919–1921.

Honjo et al., "Synthesis of the Carboxylic Analogue of Oxetanocin A", Chem. Pharm. Bull., vol. 37, pp. 1413–1415 (1989).

Norbeck et al., "Cyclobut-A and Cyclobut-G . . . ", J. Med. Chem., 1990, vol. 33, pp. 1281–1285.

Furata et al., "Asymmetric Diels–Alder Reaction . . . ", Tetrahedron Letters, vol. 27, pp. 4507–4510 (1986).

Heathcock et al., "Synthesis and Biological Evaluation . . . ", J. Med. Chem., 1989, vol. 32, pp. 197–202.

Hayashi et al., "Asymmetric [2+2]Cycloaddition . . . ", Chemistry Letters, 1990, pp. 1295–1298.

Hsiao et al., "Efficient Synthesis of Protected . . . ", Tetrahedron Letters, vol. 31, 1990, pp. 6609–6612.

Copending, commonly assigned U.S. Ser. No. 451,664 filed Dec. 18, 1989 of Bisacchi et al.

Hayashi, et al. "Asymmetric[2+2]. . . ", Chemistry Letters, 1989, pp. 793–796.

Katagiri et al., "Highly Stereoselective Synthesis". . . Chem. Phar. Bull., vol. 38, No. 1, pp. 288–290 (1990).

*Primary Examiner*—Michael L. Shippen
*Attorney, Agent, or Firm*—Stephen B. Davis

[57] ABSTRACT

Cyclobutane intermediates wherein the absolute stereochemistry is (1S,2R) of the formula

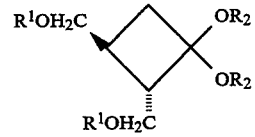

are disclosed. These intermediates are useful in the preparation of compounds having anti-viral activity.

4 Claims, No Drawings

INTERMEDIATES IN THE SYNTHESIS OF AN OPTICALLY ACTIVE CYCLOBUTANE NUCLEOSIDE

RELATED APPLICATION

This application is a divisional of Ser. No. 692,752 filed Apr. 29, 1991, now U.S. Pat. No. 5,233,076 which is a continuation-in-part of Ser. No. 528,626 filed May 24, 1990, now abandoned.

BRIEF DESCRIPTION OF THE INVENTION

The present invention relates to a process for the preparation of the optically active cyclobutanone compound of formula 1 wherein $R^3$ is a protecting group.

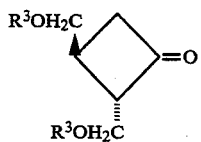

The invention relates to novel intermediates in the above process and to a process for preparing these intermediates.

The optically active cyclobutanone compound of formula 1 is an intermediate in the synthesis of the optically active cyclobutane nucleoside analog 1R-(1α,2β,3α)-2-amino-9-[2,3-bis(hydroxymethyl)cyclobutyl]-1,9-dihydro-6H-purin-6-one, represented by formula 2. Antiviral activity is exhibited by compound 2 and its

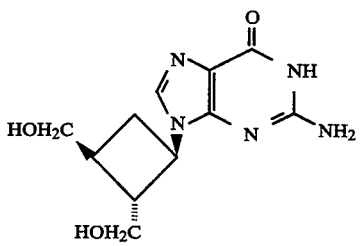

pharmaceutically acceptable salts. Unless otherwise stated, compounds 1 and 2 are optically active, and their absolute stereochemistry is (2S, 3S) and (1R, 2R, 3S), respectively as depicted in the above figures.

The preparation of compound 1 in optically active form and its conversion to optically active compound 2 has been described in Ichikawa, Y., et al., J. Chem. Soc. Chem. Commun. 1989, 1919–1921, in European patent application 358,154 published on Mar. 14, 1990, and in European patent application 366,059 published on May 2, 1990.

The preparation of compound 1 in optically inactive form (i.e., as a racemic mixture) and its conversion to optically inactive 2, (±)—(1α,2β,3α)-2-amino-9-[2,3-bis(hydroxymethyl)cyclobutyl]-1,9-dihydro-6H-purin-6-one, has been described in Slusarchyk, W. A., et al. Tetrahedron Lett. 1989, 6453–6456; in European patent application 335,355 published on Oct. 4, 1989; in Norbeck, D. W., et al. J. Med. Chem. 1990, 33, 1281–1285; and in European patent application 366,059 published on May 2, 1990. An additional preparation of optically inactive compound 1 has been described in Honjo, M., et al. Chem. Pharm. Bull. 1989, 37, 1413–1415.

DETAILED DESCRIPTION OF THE INVENTION

The process of the present invention is shown in the reaction scheme below:

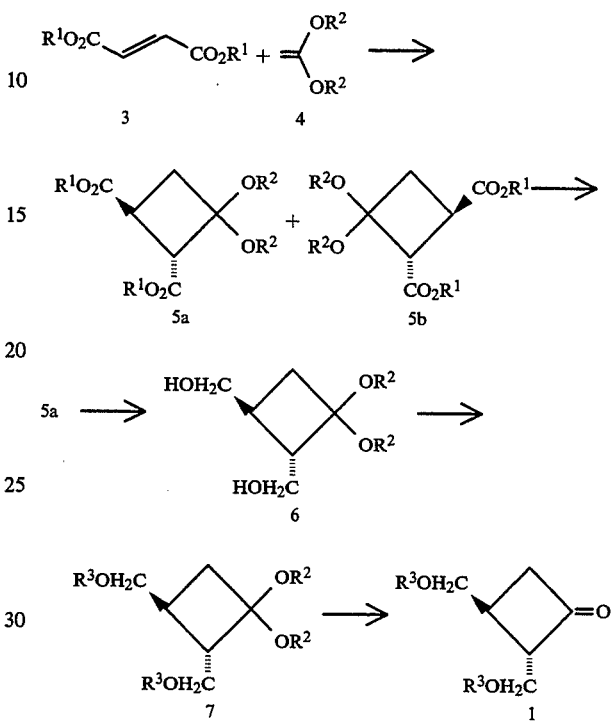

wherein $R^1$ is the group obtained by removal of the hydroxy group from the homochiral alcohol of the formula R1OH and is a branched chain alkyl of 4 to 20 carbons, a substituted straight or branched chain alkyl of 1 to 20 carbons, a substituted cycloalkyl of 3 to 20 carbons, a bridged cycloalkyl of 6 to 20 carbons, a substituted bridged cycloalkyl of 6 to 20 carbons, a polycycloalkyl of 7 to 20 carbons, a substituted polycycloalkyl of 7 to 20 carbons wherein said substituents are one or more, preferably one, two or three, selected from lower alkyl of 1 to 5 carbons, halo, lower alkoxy of 1 to 5 carbons, $$-\overset{O}{\underset{\|}{C}}-\text{lower alkoxy}$$

of 1 to 5 carbons $$-O-\overset{O}{\underset{\|}{C}}H, \quad -O-\overset{O}{\underset{\|}{C}}-\text{lower alkyl}$$

of 1 to 5 carbons and phenyl, a lactone of 4 to 6 carbons, a substituted lactone of 4 to 6 carbons wherein said lactone substituents are one or more, preferably one or two, selected from lower alkyl of 1 to 5 carbons, halo, lower alkoxy of 1 to 5 carbons, and phenyl,

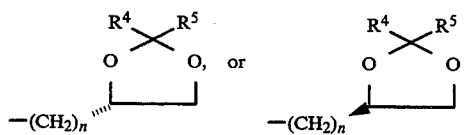

wherein n is an integer from 1 to 4, and $R^4$ and $R^5$ are independently selected from hydrogen and lower alkyl of 1 to 5 carbons;

$R^2$ is lower alkyl of 1 to 5 carbons or both $R^2$ groups are joined together by an alkylene group of 2 or 3 carbons; and $R^3$ is a protecting group.

Compounds 5a and 5b are diasteromeric relative to each other, and the absolute stereochemistry at the cyclobutane 1- and 2positions is (1S, 2R) for compound 5a and (1R, 2S), for compound 5b as depicted in the figures of the above reaction scheme. Unless otherwise stated, compounds 6 and 7 are optically active, and their absolute stereochemistry is (1S, 2S), as depicted in the figures of the above reaction scheme.

The preparation of compounds 6 and 7 in optically inactive form has previously been described in Slusarchyk, W. A., et al. Tetrahedron Lett. 1989, 6453–6456 and European patent application 335,355 published on Oct. 4, 1989.

The term "lower alkyl" refers to both straight and branched chain groups which contain from 1 to 5 carbons. Similarly, the term "lower alkoxy" refers to such lower alkyl groups attached to an oxygen. The term "halo" refers to Br, Cl, F and I.

Suitable $R^3$ protecting groups include hindered silyl groups such as t-butyldiphenylsilyl and triisopropylsilyl, acyl groups such as acetyl and benzoyl, benzyl and substituted benzyl groups such as 4-methoxybenzyl and 3,4-dimethoxybenzyl.

Suitable $R^1$ groups include

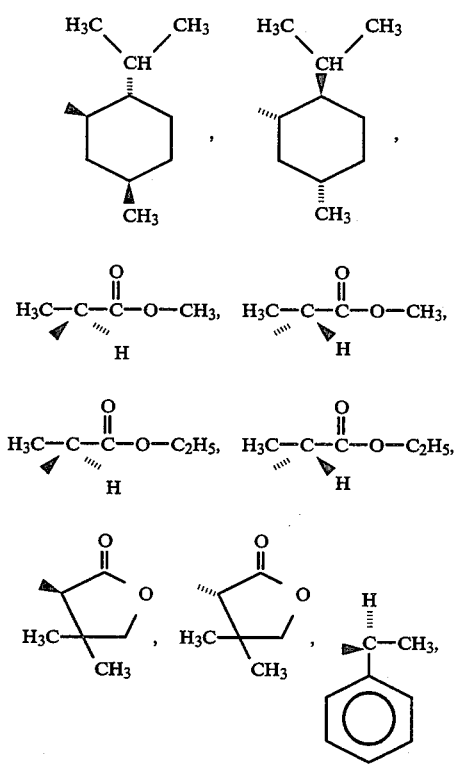

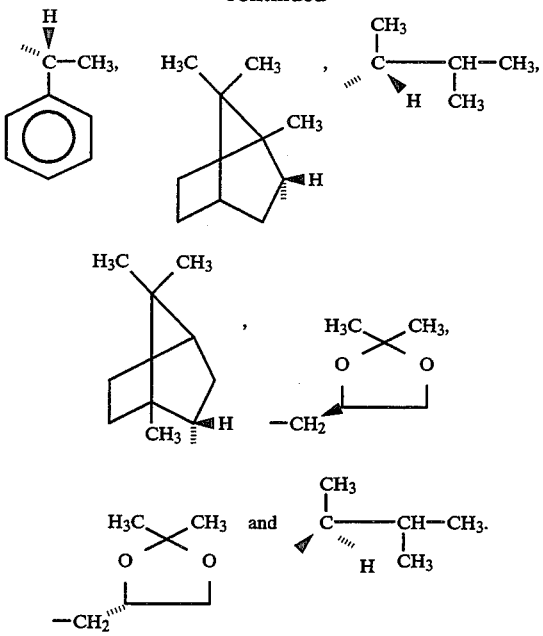

These $R^1$ groups are obtained from the optically active alcohols (+)- or (−)-menthol, (+)- or (−)-methyl- or ethyl lactate, (+)- or (−)-pantolactone, (+)- or (−)-α-phenethyl alcohol, (+)- or (−)-borneol, (+)- or (−)-α,β-isopropylideneglycerol, (+)- or (−)-3-methyl-2-butanol and the like (i.e., wherein $R^1OH$ is (+)- or (−)-menthol, (+)- or (−)-methyl or ethyl lactate, (+)- or (−)-pantolactone, (+)- or (−)-α-phenethyl alcohol, (+)- or (−)-borneol, (+)- or (−)-α,β-isopropylideneglycerol, (+)- or (−)-3-methyl-2-butanol by removal of the hydroxy group.

Preferred $R^2$ groups are methyl and ethyl.

The compound of formula 5a is prepared by reaction of a compound of formula 3 with a compound of formula 4 in the presence of a Lewis acid. Examples of such Lewis acids include aluminum compounds such as diethylaluminum chloride, diisobutylaluminum chloride, ethylaluminum dichloride, isopropoxyaluminum dichloride, aluminum trichloride and the like, boron compounds such as boron trifluoride, boron trichloride and the like, titanium compounds such as titanium tetrachloride, dichlorodiisopropoxytitanium and the like, and tin compounds such as tin tetrachloride, tin trichloride and the like. The compound of formula 3 and the compound of formula 4 are used in a proportion wherein the amount of compound 4 is 0.1 to 5 equivalents per equivalent of compound 3. The Lewis acid catalyst is used in an amount of 0.5 to 5 equivalents per equivalent of compound 3. The reaction is carried out in a solvent such as methylene chloride, toluene, hexane, petroleum ether, mixtures of toluene and hexane and the like. The reaction mixture is stirred for about 1 minute to 24 hours at a temperature of about −100° C. to 25° C. It should be noted that when the Lewis acid is titanium tetrachloride, tin tetrachloride, boron trifluoride etherate or boron tribromide then $R^1$ cannot be derived from (−)-menthol and $R^2$ cannot be methyl. In addition to 5a, varying quantities of its diastereomer 5b may also be produced in the reaction. The relative amounts of 5a and 5b produced in the reaction will depend upon the reactants, reagents, and conditions of the reaction; in particular the relative amounts of 5a and 5b will depend upon the absolute stereochemistry of the $R^1$ group chosen. The crude 5a obtained from the reaction can be purified by crystallization or by chromatography.

Preferably, the $R^1$ group for the compound of formula 3 is derived from (−)-menthol, i.e., $R^1$ is

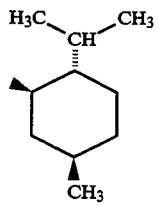

and the Lewis acid is a di(lower alkyl) aluminum chloride, particularly where each lower alkyl group is of 2 to 4 carbons. When the $R^1$ group for the compound of formula 3 is derived from (−)-menthol and the Lewis acid is a di(lower alkyl) aluminum chloride, the amount of compound 4 employed for the reaction is preferably 1 to 2 equivalents per equivalent of 3, the amount of Lewis acid employed is preferably 1.5 to 2.5 equivalents per equivalent of 3, the reaction mixture is stirred preferably for about 5 minutes to 2 hours at a temperature of preferably about −80° C. to −40° C.

Most preferably, the $R^1$ group for the compound of formula 3 is derived from (-)-menthol, the Lewis acid is diethylaluminum chloride or diisobutylaluminum chloride and $R^2$ is methyl. For example, when compound 3, wherein the group $R^1$ is derived from (−)-menthol, is reacted with 1.1 equivalents of the compound of formula 4, wherein $R^2$ is methyl, in the presence of 2 equivalents of diisobutylaluminum chloride at about −78° C. in toluene for about 30 minutes, 5a is obtained in high yield and in large excess relative to the diastereomer 5b. The resulting crude 5a is purified by chromatography on silica gel, or by crystallization from methanol or methanol-water.

A compound of formula 3 wherein $R^1$ is as defined above can be obtained commercially (e.g., the compound of formula 3 wherein $R^1$ is the group derived from the optically active alcohol (−)-menthol can be obtained from Aldrich Chemical Company) or can be readily prepared by methods known in the art (see e.g., Heathcock, C. H., et al., J. Med. Chem. 1989, 32, 197–202; Scharf, H. D., et al. Chem Ber. 1986, 119, 3492–3497; Helmchen, G. et al., DE 3702084). Compounds of formula 4 wherein $R^2$ is as defined above are either commercially available (e.g. Wiley Organics Inc.) or can be readily prepared by methods known in the art (see e.g., Organic Synthesis Collective Volume III, P. 506; S. M. McElvain J. Amer. Chem. Soc. 1955, 77, 5601–5606). The Lewis acids are commercially available or can be prepared by methods known in the art.

The compound of formula 6 is prepared by reacting a compound of formula 5a with a reducing agent such as lithium aluminum hydride, lithium borohydride, and the like, in a solvent such as tetrahydrofuran, diethyl ether, and the like. The reaction mixture is stirred for 5 minutes to 24 hours, preferably for 30 minutes to 4 hours at a temperature of 0° C. to the reflux temperature of the solvent. The compound of formula 6 is isolated and purified by methods known in the art.

A compound of formula 7 wherein $R^3$ is a protecting group is prepared by reacting a compound of formula 6 with the corresponding protecting group precursor. Suitable protecting groups $R^3$ include hindered silyl groups (such as t-butyldiphenylsilyl or triisopropylsilyl), benzyl or substituted benzyl groups, acyl groups (such as acetyl or benzoyl, preferably benzoyl) and the like. A compound of formula 7 wherein $R^3$ is a hindered silyl group is prepared by treating a compound of formula 6 with the appropriate silyl reagent e.g., the corresponding tri(hydrocarbon)silyl chloride, in a solvent such as dimethylformamide or tetrahydrofuran in the presence of a base such as triethylamine or imidazole. A compound of formula 7 wherein $R^3$ is a benzyl or substituted benzyl is prepared by treating a compound of formula 6 with a benzyl halide or a substituted benzyl halide in a solvent such as tetrahydrofuran or dimethylformamide in the presence of a suitable base such as sodium hydride. A compound of formula 7 wherein $R^3$ is an acyl group such as acetyl or benzoyl is prepared by treating a compound of formula 6 with the corresponding acyl anhydride or acyl halide, preferably benzoyl chloride or benzoic anhydride, in a solvent such as pyridine or tetrahydrofuran/triethylamine, or ethyl acetate/triethylamine, preferably ethyl acetate/triethylamine. Optionally, a catalyst such as 4,4-dimethylaminopyridine is added to the reaction mixture. The benzoylation reaction is carried out at −10° C. to 35° C., preferably at −5° C. to 25° C., ¼ hour to 48 hours, preferably ½ hour to 24 hours. Water is added to the reaction mixture, the mixture is stirred, and the product is extracted and optionally purified e.g. by chromatography.

A compound of formula 1 is prepared by treatment of a compound of formula 7 with an acid catalyst such as sulfuric acid, hydrochloric acid, p-toluenesulfonic acid, and the like, preferably sulfuric acid, in a solvent or solvent mixture such as water, water-acetonitrile, water-dioxane, acetone and the like, preferably water-acetonitrile. The reaction mixture is stirred at 0° C. to 60° C., preferably at 15° C. to 30° C. for ½ hour to 48 hours, preferably for 2 hours to 24 hours. The reaction mixture is neutralized and the product is extracted and optionally purified by e.g. chromatography or crystallization.

The following examples are specific embodiments of the invention.

EXAMPLE 1

(1S-Trans)-3,3-Dimethoxy-1,2-Cyclobutane-Dicarboxylic Acid, Di-(−)-Menthyl Ester Di-(−)-menthylfumarate (100 g) was dissolved in 400 ml dry toluene and cooled to −75° C. under argon. To this solution was added with stirring diisobutylaluminum chloride (99.5 ml) over 15 minutes. The resulting orange mixture was stirred at −75° C. for 15 minutes and 1,1-dimethoxyethylene (24.7 g) was added over 15 minutes. After stirring the reaction mixture for 10 minutes at −78° C., methanol (30 ml) was added over 15 minutes and the mixture was stirred for 30 minutes. Hexane (250 ml) was added over 5 minutes followed by the addition of 20% aqueous sodium hydroxide (40 ml) over 15 minutes at −60° C. to −40° C. The reaction mixture was slowly (over 45 minutes) allowed to warm to 10° C. and anhydrous magnesium sulfate (40 g) was added. The mixture was allowed to come to room temperature, was filtered, and the filtrate was concentrated in vacuo to afford an oil (119.5 g) which solidified under vacuum. The crude product was recrystallized from methanol-water (95:5) to afford 102g of the title compound (isomerically pure as judged by HPLC) as a white solid, m.p. 89° C., $[\alpha]_D = -28.5°$ (c=1, CHCl$_3$).

Alternatively, the title compound can be prepared by using diethylaluminum chloride instead of diisobutylaluminum chloride, as described below.

A solution of diethylaluminum chloride (1M in hexane, 5.1 ml) was added dropwise to a stirred solution of di-(−)-menthyl fumarate (1.0 g) in 5 ml toluene under nitrogen at −78° C. The reaction mixture was stirred at that temperature for 15 minutes, followed by the addition of 0.247 g 1,1-dimethoxyethylene. The reaction mixture was stirred at −78° C. for 30 minutes, then was carefully added to a mixture of 50 ml hexane and 20 ml saturated aqueous sodium bicarbonate solution. The organic phase was washed with additional saturated sodium bicarbonate solution (2×20 ml), water (3×20 ml), and was dried (magnesium sulfate) and concentrated in vacuo giving 1.23 g of a thick oil. The crude mixture was recrystallized from methanol-water (95:5) affording 0.98 g of the title compound pure by HPLC and NMR.

EXAMPLE 2

(1S-trans)-3,3-Dimethoxy-1,2-cyclobutane-dimethanol

A solution of (1S-trans)-3,3-dimethoxy-1,2cyclobutanedicarboxylic acid, di-(−)-menthyl ester (3.5 g) in 15 ml dry tetrahydrofuran was added dropwise over 5 minutes to a suspension of 420 mg of lithium aluminum hydride in 73 ml of dry tetrahydrofuran at room temperature and under argon. The mixture was heated at 55° C for 1 hour, after which no starting material was observed by thin layer chromatography. To the reaction mixture, cooled to 5° C., was added sequentially 420 μl water, 420 μl of 15% aqueous sodium hydroxide, and 1.28 ml of water. The resulting suspension was stirred for 15 minutes at room temperature, then ca. 5g of anhydrous magnesium sulfate was added, and stirring was continued an additional 0.5 hour. The solids were removed by filtration through Celite, and the clear, colorless filtrate was concentrated to afford 3.7 g of a semi-solid residue (a mixture of the title compound and (−)-menthol). This residue was dissolved in a mixture of 35 ml water, 3.5 ml methanol and 20 ml heptane. The organic layer was separated and the aqueous layer was extracted with additional heptane (3×10 ml). The combined organic fractions were washed once with 5 ml of water. The combined aqueous fractions were concentrated in vacuo to ca. 5 ml, saturated with sodium chloride, and extracted with ethyl acetate (2×20 ml). The combined ethyl acetate extracts were dried over anhydrous magnesium sulfate and concentrated to afford 1.33 g of the title compound as a clear colorless oil. $^1$HNMR (CDCl$_3$):δ1.69 (ddd, 1H, J=1.2, 7.8, 12.3 Hz, H-4); 2.1 (m, 1H, H-3); 2.35 (m, 2H, H-2 and H-4); 2.64 (s, 2H, 2×OH); 3,184 (s, 3H, OCH$_3$); 3,188 (s, 3H, OCH$_3$); 3.51 (dd, 1H, J=8.8, 10.5 Hz) and 3.75 (m, 3H) [2×OCH$_2$].

Alternatively, the above-described crude semi-solid mixture of the title compound and (−)-menthol can be treated as follows. The crude mixture resulting from the lithium aluminum hydride reduction of 17.5 g of (1S-trans)-3,3-dimethoxy-1,2-cyclobutanedicarboxylic acid, di-(−)-menthyl ester was dissolved in 100 ml of heptane and was washed with water (4×50 ml). The combined aqueous fractions were washed with 25 ml of heptane, then were saturated with ammonium sulfate (45g) and were extracted with ethyl acetate (4×50 ml). The combined ethyl acetate extracts were dried over anhydrous magnesium sulfate and concentrated to afford 6.3 g of the title compound as a colorless oil.

EXAMPLE 3

(1S-trans)-3,3-Dimethoxyl,2-cyclobutane-dimethanol, dibenzoate ester

To a solution of 300 mg of (1S-trans)-3,3-dimethoxy-1,2-cyclobutanedimethanol in 3.4 ml of dry pyridine at 5° C. under argon was added dropwise 494 μl of benzoyl chloride. The mixture was stirred with cooling for an additional 1.5 hours after which 100 μl water was added. The reaction mixture was diluted with ethyl acetate and washed with 10% aqueous hydrochloric acid, brine, saturated sodium bicarbonate and brine. The organic solution was dried over anhydrous magnesium sulfate and concentrated to afford 642 mg of the title compound as a clear, colorless oil. An analytical sample of the title compound was prepared by semi-preparative HPLC, $[\alpha]_D = 54.3°$ (c=0.94, CHCl$_3$).

Alternatively, a solution 147.7 g. of (1S-trans)-3,3-dimethoxy-1,2-cyclobutanedimethanol in 900 ml. of ethyl acetate, chilled in an ice bath to an internal temperature of 8° C., was treated with 410 g. of benzoic anhydride, 211 g. of triethylamine, and 6.5 g. of 4,4-dimethylaminopyridine. The stirred mixture was allowed to come to room temperature over 15 hours. The mixture was then treated with 45 ml. of water and stirred at room temperature for 6 hours. The mixture was diluted with 1 L of ethyl acetate and washed with water (2×1 L), 1N HCl (2×0.5 L), water (0.5 L), 10% sodium bicarbonate (2×0.5 L), and brine (0.5L). The organic solution was dried over anhydrous magnesium sulfate and was concentrated to afford 309.2 g. of the title compound.

EXAMPLE 4

(2S-trans) -2,3-Bis[(benzoyloxy)methyl]-cyclobutanone

A solution of (1S-trans)-3,3-dimethoxy-1,2-cyclobutanedimethanol, dibenzoate ester (312 mg) in 12 ml of acetonitrile and 3.8 ml of 0.5N aqueous sulfuric acid was stirred at room temperature overnight. An additional 1.9 ml of 0.5N aqueous sulfuric acid was added and stirring was continued for an additional 6 hours, after which no starting material remained by thin layer chromatography. The solution was diluted with ethyl acetate and was washed with brine, saturated aqueous sodium bicarbonated and brine. The organic solution was dried over anhydrous magnesium sulfate and was concentrated to afford 245 mg of the title compound as a white solid. An analytical sample of the title compound was recrystallized from methylene chloride-ether, m.p. 95.5–97° C., $[\alpha]_D = 24.1°$ (c=1.31, CHCl$_3$).

What is claimed is:

1. A compound of the formula

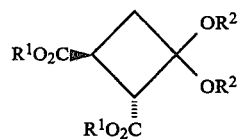

wherein the absolute stereochemistry at the cyclobutane is (1S, 2R) and

R$^1$ is

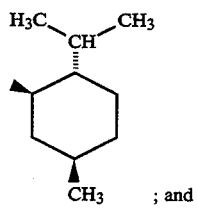 ; and
$R^2$ is lower alkyl of 1 to 5 carbons or both $R^2$ groups are joined by an alkylene group of 2 or 3 carbons.
2. A compound according to claim 1 wherein $R^2$ is methyl or ethyl.
3. A compound according to claim 2 wherein $R^2$ is methyl.
4. A compound according to claim 1, (1S-trans)-3,3-dimethoxy-1,2-cyclobutanedicarboxylic acid, di-(—)-menthyl ester.
* * * * *